United States Patent
Pillai et al.

(10) Patent No.: US 10,466,244 B2
(45) Date of Patent: Nov. 5, 2019

(54) METHODS AND MATERIALS FOR IDENTIFYING THERAPEUTIC RESPONSE IN CHRONIC MYELOID LEUKEMIA

(71) Applicant: RAJIV GANDHI CENTRE FOR BIOTECHNOLOGY, Thiruvananthapuram (IN)

(72) Inventors: Madhavan Radhakrishna Pillai, Thiruvananthapuram (IN); Mani Shankar Babu, Thiruvananthapuram (IN); Praveen Kunjan Sobhan, Thiruvananthapuram (IN); Anand Krishnan, Thiruvananthapuram (IN); Mahendra Seervi, Ajmer Dist. (IN); Rakesh Sathish Nair, Thiruvananthapuram (IN)

(73) Assignee: RAJIV GANDHI CENTRE FOR BIOTECHNOLOGY, Kerala (IN)

( * ) Notice: Subject to any disclaimer, the term of this patent is extended or adjusted under 35 U.S.C. 154(b) by 117 days.

(21) Appl. No.: 15/481,213

(22) Filed: Apr. 6, 2017

(65) Prior Publication Data
US 2018/0299449 A1 Oct. 18, 2018

Related U.S. Application Data

(63) Continuation of application No. PCT/IN2014/000168, filed on Mar. 14, 2014.

(30) Foreign Application Priority Data

Mar. 15, 2013 (IN) ........................ 1119/CHE/2013

(51) Int. Cl.
*G01N 33/53* (2006.01)
*G01N 33/574* (2006.01)
*C07D 401/12* (2006.01)
*C07D 405/14* (2006.01)
*G01N 33/558* (2006.01)

(52) U.S. Cl.
CPC ..... *G01N 33/57426* (2013.01); *C07D 401/12* (2013.01); *C07D 405/14* (2013.01); *G01N 33/558* (2013.01); *G01N 2333/82* (2013.01); *G01N 2800/52* (2013.01)

(58) Field of Classification Search
CPC ........... G01N 33/57426; G01N 33/558; G01N 2333/82; G01N 2800/52; G01N 33/53; C07D 401/12; C07D 405/14
See application file for complete search history.

(56) References Cited

U.S. PATENT DOCUMENTS

| | | | |
|---|---|---|---|
| 4,208,479 A * | 6/1980 | Zuk | C07J 41/0016 435/7.72 |
| 2011/0045608 A1 * | 2/2011 | Salamone | G01N 33/531 436/528 |
| 2012/0277109 A1 * | 11/2012 | Singh | G01N 33/5011 506/9 |

FOREIGN PATENT DOCUMENTS

RU 229633 * 3/2007 ............. G01N 33/53

OTHER PUBLICATIONS

Quintas et al. (Mayo Clinic Proceedings;2006; 81,7:973).*

* cited by examiner

*Primary Examiner* — Julie Wu
*Assistant Examiner* — Carmencita M Belei
(74) *Attorney, Agent, or Firm* — Mannava & Kang, P.C.; Vinay Malik

(57) ABSTRACT

This document provides methods and materials for identifying individuals with protein tyrosine kinase associated disorders for responsiveness to a kinase inhibitor (e.g., imatinib or nilotinib). For example, methods and materials for using a chemi-immunochromatographic lateral flow strip for detection of BCR-ABL and drug resistance are provided.

3 Claims, 7 Drawing Sheets

Presence of control indicates assay is working. Sample has both imatinib and nilotinib resistance. Patient will not resopnd to imatinib or nilotinib thearpy.

Figure 5B

Sample has both imatinib sensitivity. Patient will respond to imatinib therapy.

Figure 5C

Sample has imatinib resistance but nilotinib sensitivity. Patient will respond nilotinib but not to imatinib.

Figure 5D

Sample has imatinib sensitivity and resistance and nilotinib sensitivity. Patient will likely not respond most effectively to imatinib therapy but should respond to nilotinib therapy.

Figure 6F

METHODS AND MATERIALS FOR IDENTIFYING THERAPEUTIC RESPONSE IN CHRONIC MYELOID LEUKEMIA

TECHNICAL FIELD

This document relates to methods and materials for identifying therapeutic response in chronic myeloid leukemia (e.g., response to imatinib and/or nilotinib). For example, this document relates to methods and materials for using a chemi-immunochromatographic lateral flow strip with immobilized drug for detection of BCR-ABL and therapeutic response.

BACKGROUND INFORMATION

Chronic myeloid leukemia (CML) is a form of cancer characterized by the increased proliferation and accumulation of myeloid cells in the bone marrow and blood. CML represents 14% of all leukemia cases and 33,400 new cases of CML were reported in 2004. CML is associated with chromosomal translocation between chromosome 9 and 22 resulting in formation of characteristic Philadelphia chromosome. Pathologically significant end product of chromosomal translocation is fusion of two genes, BCR (breakpoint cluster region) gene from chromosome 22 and ABL gene on chromosome 9. This abnormal fusion results in formation of chimera and constitutively active protein known as BCR-ABL, a tyrosine kinase receptor which is responsible for uncontrolled cell cycle and other cancer related biological features. BCR-ABL thus plays a role in induction of cancer during CML and hence acts as a therapeutic target of CML (Bartram, et al., *Nature*, 306:277 (1983)).

A series of inhibitors, based on the 2-phenylaminopyrimidine class of pharmacophores, has been identified that have exceptionally high affinity and specificity for ABL (Zimmerman, et al., *Med. Chem. Lett.*, 7:187(1997)). Imatinib mesylate (also known as STI-571 and Gleevec) is an orally bioavailable 2-phenylaminopyrimidine with targeted inhibitor activity against the constitutively active tyrosine kinase of the BCR-ABL chimeric fusion protein (Quintás-Cardama, et al., *Mayo Clin. Proc.*, 81:973 (2006)). Nilotinib (also known as AMN107) is a phenylamino-pyrimidine derivative with a 20- to 30-fold increased potency compared with imatinib against BCR-ABL. This may be due to a better fit within the ABL kinase pocket. However, nilotinib, like imatinib, only binds the ABL protein in its inactive conformation. Imatinib has become the first drug of choice CML treatment. Despite the success of imatinib and nilotinib, a significant number of patients (10-30%) have demonstrated poor initial response (Drucker, et al., *Nature Med.* 2:561 (1996)). During the course of the disease, some percentage of CML patients develops mutations in the ATP binding domain of the BCR-ABL tyrosine kinase which make them resistant to imatinib therapy. Because of the tighter binding to BCR-ABL, nilotinib can be used for treatment of patients who respond weakly to imatinib or imatinib resistant patient. However in some cases, patients may develop resistance to both nilotinib and imatinib. Discovery of resistance to imatinib and nilotinib therapy has led to the emergence of new drugs and therapeutic strategies. Therefore, there is significant need to develop means of rapidly monitoring the effects of imatinib or nilotinib at early stages.

Identification of BCR-ABL mutants that are resistant to imatinib and/or nilotinib has become an integral part of patient care management in CML therapy yet current diagnostic and prognostic tools are too expensive, time consuming, and require highly skilled labor. The approach described herein is a rapid, easy-to-use immunochromatography-based testing method utilizing drug immobilization to detect drug-protein interactions.

SUMMARY

This document relates to methods and materials for identifying therapeutic response to one or more drugs in chronic myeloid leukemia (e.g., response to imatinib and/or nilotinib). For example, this document relates to methods and materials for using a chemi-immunochromatographic lateral flow strip for simultaneous detection of BCR-ABL and therapeutic response.

This document generally relates to methods and materials for the detection of drug response via drug-protein interaction. Proteins include fusion proteins and/or their mutant forms, including those resulting from a chromosomal translocation. In particular, methods and materials are provided for identifying BCR-ABL fusion proteins and determining therapeutic response in chronic myeloid leukemia (e.g., response to imatinib and/or nilotinib). Response to a therapy is monitored using methods and materials of the invention, and in other aspects a disease such as cancer is predicted, diagnosed, and/or prognosticated. In specific embodiments, the methods and materials are utilized to predict response or prognosis of an individual having disease or suspected of having disease and monitor efficacy and response of a therapy.

In certain aspects, detection of fusion proteins and/or their mutant forms, including those resulting from a chromosomal translocation.

In specific aspects, the methods and compositions of the invention are employed to monitor fusion protein activity and/or level. For example, this document relates to methods and materials for using a chemi-immunochromatographic lateral flow strip for simultaneous detection of BCR-ABL mutant and drug sensitivity.

As described herein, a kit can be used for detecting drug resistance in disease, wherein the kit comprises a substrate comprising at least one immobilized drug and a reagent comprising a labeled binding agent that binds to the drug target. In some cases, the drug can be imatinib and in other cases the drug can be nilotinib. If two drugs are immobilized, the first drug can be imatinib and the second drug can be nilotinib. In addition to an immobilized drug, the substrate can further comprise an immobilized antibody. The labeled binding agent that binds to the drug target can be a labeled DNA aptamer, RNA aptamer, protein aptamer, antibody, antibody fragment, binding polypeptide, binding peptide, or combinations thereof. In some cases the drug target is BCR-ABL and the disease is chronic myeloid leukemia.

As further described herein, a method can be used for identifying therapeutic resistance in a patient suffering from a disease, wherein the method comprises obtaining a test sample from the patient, combining the test sample with a reagent that comprises a labeled binding agent capable of binding the drug target, incubating the test sample and the reagent to allow the labeled binding agent to bind the drug target, delivering the incubated sample to a substrate comprising an immobilized drug, and visually detecting a line on the substrate if the labeled binding agent bound to drug target binds to the immobilized drug, wherein detection of said line indicates that the patient is not resistant to said drug. The drug can be imatinib or nilotinib.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The terms "cancer", "cancerous", or "malignant" refer to or describe the physiological condition in mammals that is typically characterized by unregulated cell growth. Examples of cancer include but are not limited to, leukemia, lymphoma, blastoma, carcinoma and sarcoma. More particular examples of such cancers include chronic myeloid leukemia, acute lymphoblastic leukemia, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma, cervical cancer, stomach cancer, bladder cancer, hepatoma, breast cancer, colon carcinoma, and head and neck cancer.

The term "chromosomal translocation" as used herein refers to an event wherein a fragment of one chromosome is broken off and is then attached to another chromosome, which may be of a different pair, in specific embodiments. In specific aspects of translocations of the invention, the molecules are tumor-specific because the chimeric RNA and subsequent protein product only reside in the cell with the chromosomal translocation, which is beneficial for diagnostic and therapeutic applications. In alternative embodiments, translocations that result in enforced proto-oncogene expression do not provide cell-specific diagnostic because the proto-oncogene is also expressed in normal cells. The translocations are generally between non-homologous chromosomes but can be between homologous chromosomes. In particular, the fusion gene products generated by the chromosomal translocation are intracellularly located. Polynucleotides (which may be referred to herein as genes) that may be affected by chromosomal translations include gene fusions wherein the breakpoints reside within introns of the affected genes on the two chromosomes of concern, for example.

The term "fusion protein" as used herein refers to a polypeptide encoded by a polynucleotide wherein the polynucleotide is the result of fusion between at least two polynucleotides, such as from two different genes, including the polynucleotides that result upon chromosomal translocation. In other words, the fusion protein comprises at least two different regions: one region encoded from one polynucleotide or gene and a second region encoded from another polynucleotide or gene. For example, the fusion protein can be BCR-ABL.

Figure 3:
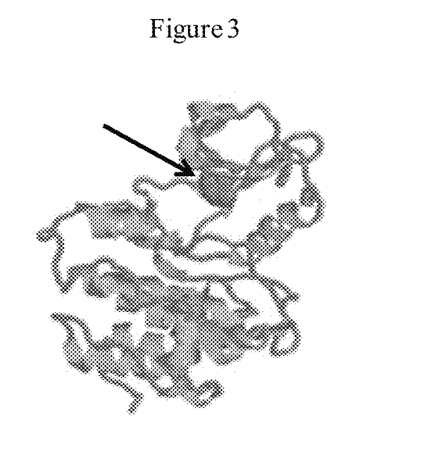
FIG. 3 is a picture of the crystal structure of BCR-ABL kinase domain showing the position of the T315 gatekeeper amino acid (arrow), which is frequently mutated in imatinib or nilotinib resistant CML.

The term "mutant" or "mutant form" as used herein refers to changes in the protein that disrupt the binding site where a therapeutic drug would normally bind. These changes result in reduced binding affinity for the therapeutic and confer therapeutic resistance. Mutations resulting in a mutant protein include, but are not limited to, alterations in the nucleic acid sequence, alterations in the amino acid sequence, and post-translational modifications. Post-translational modifications can include phosphorylation, farnesylation, acetylation, glycosylation, sumoylation, myristylation, alkylation, glutamylation, glycylation, isoprenylation, lypoylation, phosphopantetheinylation, sulfation, selenation, ubiquitination, citrullination, deimination, deamidation, or combinations thereof. Mutations in BCR-ABL amino acid sequence known to alter the drug binding pocket and hence the ability for the protein to bind the therapeutic includes mutations at the position of the gatekeeper amino acid, threonine 315, shown in FIG. 3 (T315 indicated by arrow). For example, mutations at threonine 315 include, but are not limited to, T315I. Other mutations in the BCR-ABL amino sequence that can alter therapeutic binding affinity may include D233, T243, M244, K245, G249, G250, G251, Q252, Y253, E255, V256L Y257, F259, K262, D263, K264, 5265, V268, V270, T272, Y274, D276, T277, M278, E282, F283, A288, M290, K291, E292, 1293, P296, L298, V299, Q300, G303, V304, C305, T306, F311, T315, E316, F317, M318, Y320, G321, D325, Y326, L327, R328, E329, Q333, E334, A337, V339, L342, M343, A344, 1347, A350, M351, E352, E355, K357, N358, F359, 1360, L364, E373, N374, K378, V379, A380, D381, F382, T389, T392, T394, A395, H396, A399, P402, or T406. The current invention is designed to determine if the sample contains BCR-ABL with mutations that result in lower binding affinity to the therapeutic.

The terms "treating", "treatment", "drug", and "therapy" as used herein refer to curative therapy, prophylactic therapy, and preventative therapy. The terms "individual selected for treatment" refer to an individual who has been identified as having a condition that artisans understand can respond to a specific therapy and, consequentially is being considered for treatment (or being treated with) that therapy.

Figure 1A:
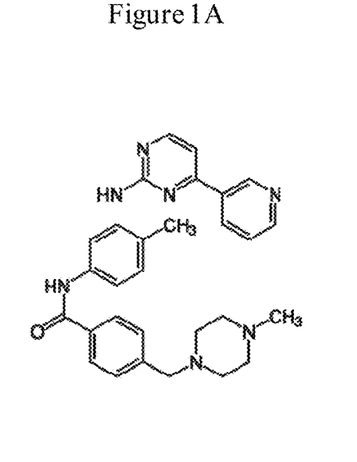
FIG. 1A is a picture of the chemical structure of imatinib.
Figure 1B:
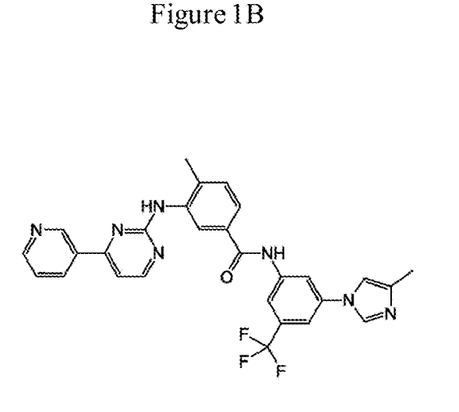
FIG. 1B is a picture of the chemical structure of nilotinib.

In a preferred embodiment, the therapeutic drug is imatinib or nilotinib, the chemical structures of which are shown in FIGS. 1A and 1B).

The term "resistance" or "resistant therapy" as used herein refers to a medical condition in an individual that is not responsive to a therapy. In specific embodiments, the terms refer to cancer that is resistant to a cancer therapy or becomes resistant to a cancer therapy. In certain embodiments, the terms may be further defined as concerning a cancer wherein cancer cells are not killed by the therapy or even may proliferate during the therapy treatment or shortly thereafter, such as within months, weeks, or days. In specific embodiments, the terms may be further defined as a protein lacking the ability to bind the therapeutic, for example the BCR-ABL fusion protein unable to bind to imatinib and/or nilotinib). The resistance may be de novo resistance or acquired resistance.

The term "sample" as used herein refers to a representative entity from any organism, including humans, animals, and plants, as well as cell cultures, recombinant cells, cell components, and environmental sources, for example. They may comprise a biological tissue, fluid, or specimen. Samples may be obtained from any animal, including, a mammal, for example, human, horse, dog, cat, sheep, goat, cow, and pig. In a preferred embodiment, the mammal is a human. Samples may include, but are not limited to, amniotic fluid, blood, blood cells, cerebrospinal fluid, fine needle biopsy samples, peritoneal fluid, plasma, pleural fluid, saliva, semen, serum, sputum, tissue or tissue homogenates, tissue culture media, urine, and the like. Samples may also be processed, such as sectioning of tissues, fractionation, purification, or cellular organelle separation. Preferred samples include blood, plasma, and bone marrow. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

Figure 2A:
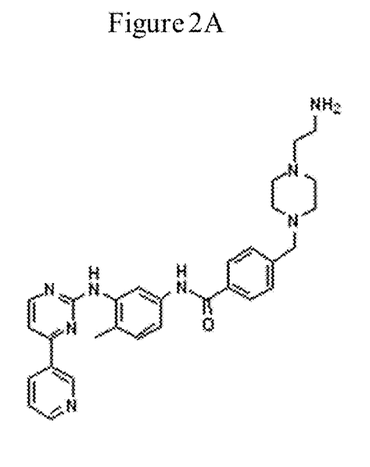
FIG. 2A is a picture of the chemical structure of amino-modified imatinib.
Figure 2B:
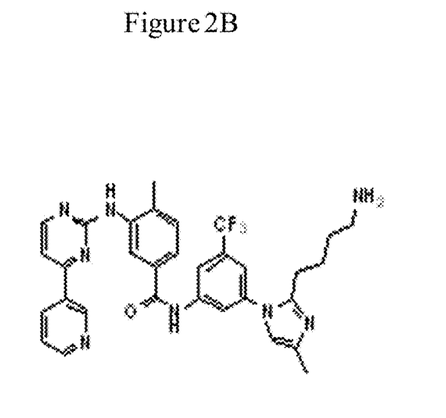
FIG. 2B is a picture of the chemical structure of amino-modified nilotinib.
Figure 2C:
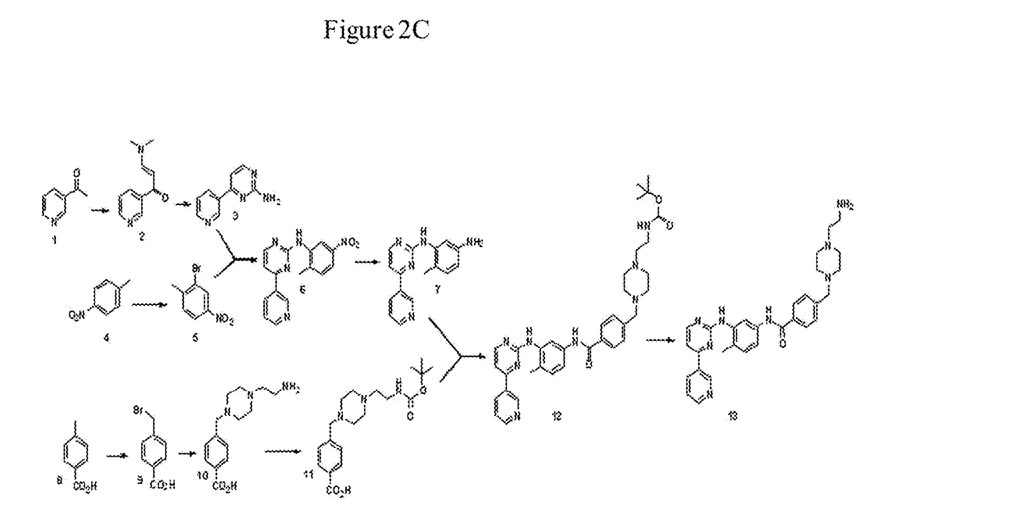
FIG. 2C is a picture of the synthesis scheme of amino-modified imatinib.
Figure 2D:
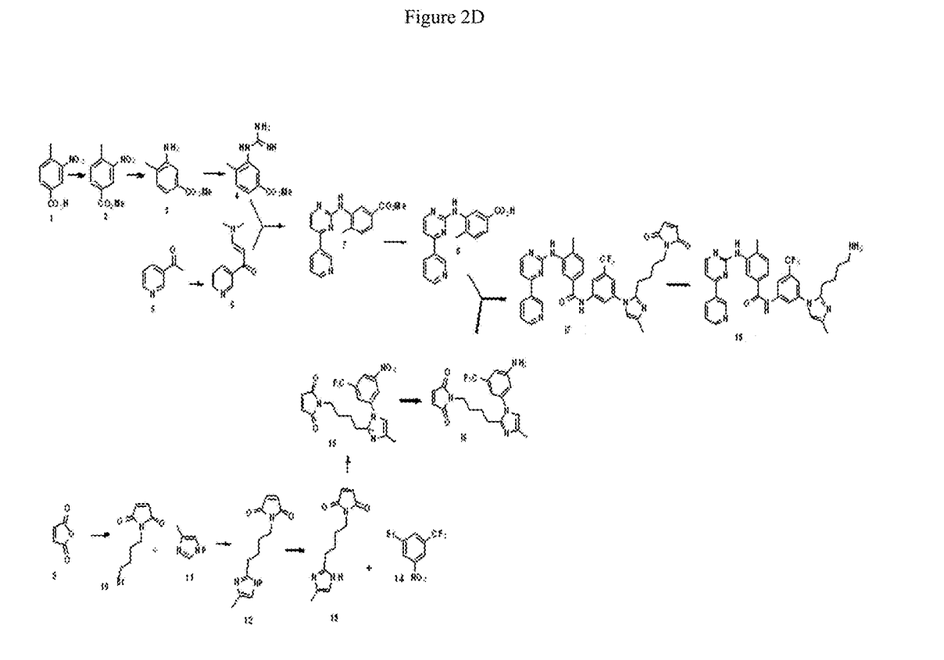
FIG. 2D is a picture of the synthesis scheme of amino-modified nilotinib.
Figure 4:
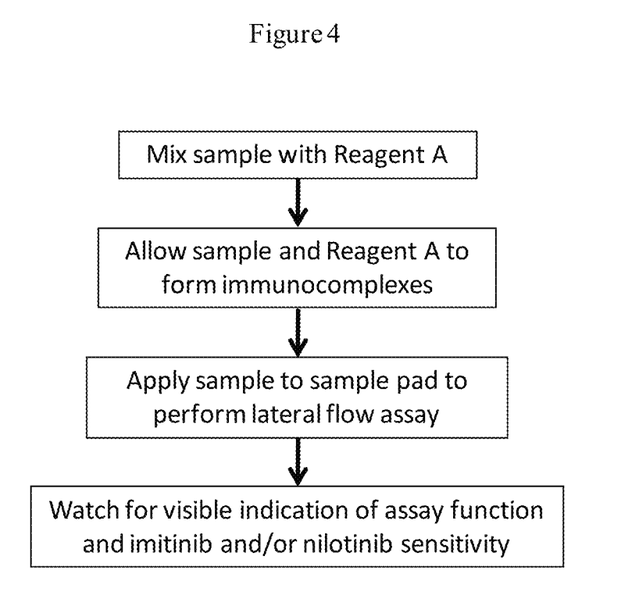
FIG. 4 is a flow chart of an exemplary process for the detection of imatinib and/or nilotinib resistance.
Figure 5A:
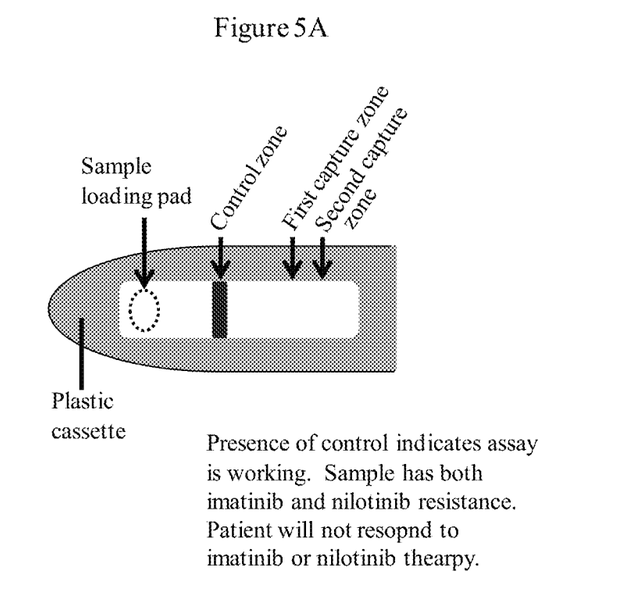
FIGS. 5A-D are schematics of the various outcomes of the lateral flow assay.
Figure 5B:
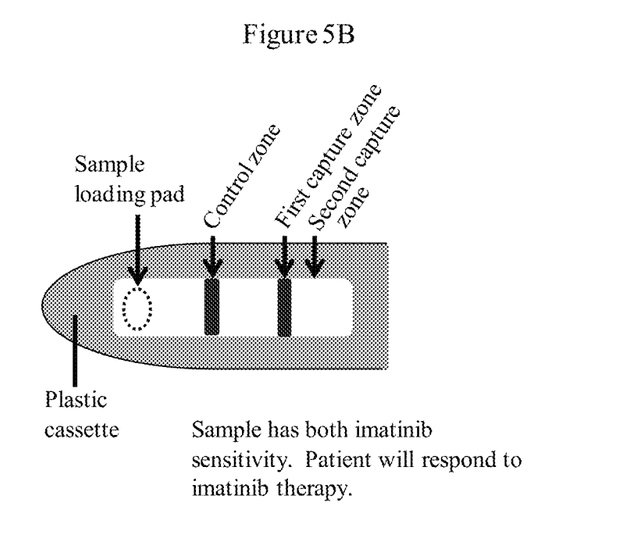
Figure 5C:
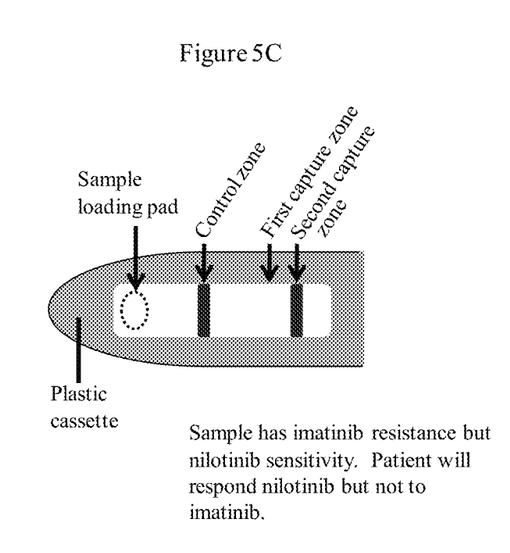
Figure 5D:
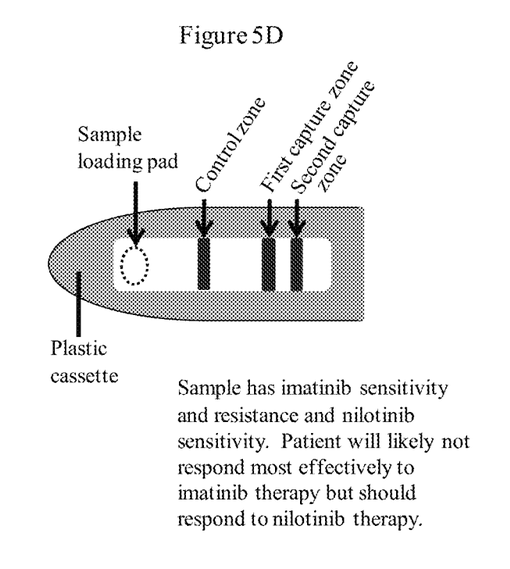

FIG. 4 outlines an exemplary process for detecting protein binding to therapeutic. The therapeutic drug is immobilized on a substrate. There are a variety of methods to attach probes to a substrate, although in particular aspects the attachment is chemical, such as a covalent attachment between the drug and the substrate, although non-covalent attachments may be employed. In further specific embodiments, the attachment of the drug to the substrate is via an amino-modification on the drug. FIGS. 2A and 2B show the chemical structure of amino-modified imatinib and nilotinib, respectively. Although an amino-modification is shown, it should be understood that other chemistries could be used to attach the drug to the substrate. For example maleimide, amidation, and alkylation with iodoacetamide are examples of other modifications. If modifying a drug containing sulfur, the modification could involve treatment with methanethiosulfonates. FIGS. 2C and 2D show the chemical synthesis pathways that were followed to generate the amino-modified imatinib and nilotinib, respectively. Amino-linkers of other lengths could also be used to modify the drugs in order to attach the drug to the substrate.

The substrate can be made of any kind so long as it is suitable for immobilization of the drug of interest and so long as it is suitable for being subjected to a sample comprising a protein. Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride, or nanotubes and nanofibers made of materials like carbon and thereof. In a preferred embodiment, the substrate is nitrocellulose membrane.

As shown in FIG. 4, the initial step comprises combining the test sample with Reagent A in a reaction vessel. Reagent A comprises a hypotonic potassium chloride (KCl) solution that helps in the lysis of blood cells and release of cellular contents. Reagent A further comprises a labeled binding agent to detect the therapeutic target. The labeled binding agent binds to both mutant and wild type forms of the therapeutic target. The labeled binding agent should be selected such that the labeled binding agent binding site does not interfere with the therapeutic binding site. In a preferred embodiment, the labeled binding agent is a gold-conjugated antibody that binds BCR-ABL. Reagent A may further comprise labeled binding agents that bind to other proteins that can be utilized as positive controls. If the therapeutic(s) also have an affinity to these control protein, their detection serves two purposes. First, their visible presence is a positive control that the assay is working. Second, by capturing them as a control, this prevents non-specific therapeutic binding that would otherwise appear as false positive. For example, in the case of the therapeutic drug imatinib, platelet derived growth factor receptor (PDGFR) and c-tyrosine kinase receptor (c-kit) exhibit specific affinity for imatinib. If antibodies are used as the binding agent, the antibodies used against the positive controls must be raised in a different species than the antibody used against the therapeutic target. The reasons for doing so will become clear as the methods are further explained below. In a specific embodiment, Reagent A comprises KCl, gold-conjugated anti-BCR-ABL antibody (raised in mouse), gold-conjugated anti-PDGFR antibody (raised in rabbit), and gold-conjugated anti-c-kit antibody (raised in rabbit). Alternatively, the anti-BCR-ABL antibody could be raised in rabbit and the anti-PDGFR and anti-c-kit antibodies could be raised in mouse. Other species antibodies could be raised in include, but are not limited to, goat, horse, rabbit, pig, and donkey.

After the sample has been mixed with Reagent A, the mixture is allowed to incubate at room temperature for a specified period of time. For example, the incubation period could be 1 minute, 2 minutes, 3 minutes, 4 minutes, 5 minutes, 10 minutes, or up to 60 minutes. The preferred incubation period is 15 minutes. The incubation period allows for the binding agents in Reagent A to bind to their respective targets. If the binding agents are antibodies, they will bind to their antigen, forming an immunocomplex. A visual indicator may optionally be incorporated to determine if immunocomplexes have formed. For example, the visual indicator may involve a horseradish peroxidase system that is well known in the art. After the desired incubation period, the mixture is applied onto a sample pad on the test strip.

Detection of the immunocomplexes may be carried out using, for example, a lateral flow assay. Such lateral flow assays have the potential to be a cost-effective, fast, simple, and sensitive method, for instance for on-site screening assays. The lateral flow assay comprises a substrate that allows a lateral flow to occur wherein either the sample is displaced from one location on the substrate to another. An example of a lateral flow test strip of the invention comprises, for example, the following components:

Sample pad—an absorbent pad onto which the test sample is applied.

1. Reaction membrane/substrate—a hydrophobic nitrocellulose or cellulose acetate membrane onto which drugs are immobilized in a line across the membrane as a capture zone or test line (a control zone may also be present, containing antibodies specific for the conjugate antibodies).
2. Wick or waste reservoir (optional)—a further absorbent pad designed to draw the sample across the reaction membrane by capillary action and collect it.

After the sample is placed onto the sample pad, the sample migrates from the sample pad through the reaction membrane. The sample then continues to migrate across the membrane until it reaches an optional control zone, where control protein/labeled antibody conjugate binds to immobilized antibodies. This control line serves as a positive control for the assay and can also remove antigens likely to interfere with the test. It is important to note that the immobilized antibodies only bind the control protein/labeled antibody conjugates since the immobilized antibodies are specific to the species in which the labeled antibody was raised. The sample migrates further along the strip until it reaches the capture zone, where the therapeutic target/labeled antibody conjugate complex binds to the immobilized drug producing a visible line on the membrane. In some cases, only one drug is immobilized on the membrane. In some cases, there are two capture zones, where two different drugs can be immobilized on the membrane at each capture zone. In other cases, more than two drugs can be immobilized on the membrane resulting in more than two capture zones.

In specific embodiments, the sample is mixed with Reagent A, which comprises hypotonic KCl, gold-conjugated anti-BCR-ABL antibody that was raised in mouse, gold-conjugated anti-c-kit antibody raised in rabbit, and gold-conjugated anti-PDGFR antibody raised in rabbit. The sample is incubated to allow for the gold-labeled antibodies to bind to their respective antigens. The sample is then placed onto the sample pad and migrates to the control zone. The control zone is a strip on the reaction membrane with immobilized anti-rabbit antibodies. At this point, any PDGFR/gold-conjugated anti-PDGFR antibody and c-kit/gold-conjugated anti-c-kit antibody will bind. The visible gold-conjugated antibodies concentrated at the control zone indicate that the assay is working. The sample migrates further along the strip, reaching the first capture zone. The first capture zone contains immobilized imatinib and will bind BCR-ABL/gold-conjugated anti-BCR-ABL antibody. The visibility of the first capture zone indicates that imatinib is able to bind BCR-ABL and the patient is not resistant to imatinib therapy. The sample continues to migrate further along the strip, reaching the second capture zone. The second capture zone contains immobilized nilotinib and will also bind BCR-ABL/gold-conjugated anti-BCR-ABL antibody. The visibility of the second capture zone indicates that nilotinib is able to bind BCR-ABL and the patient will be responsive to nilotinib therapy. If both the capture zones are visible, this indicates that the patient will respond to either imatinib therapy or nilotinib therapy. Formation of color in the reaction is dependent on the presence of gold-conjugated antibody and non-specific interactions, if any, will be undetected with no positive results. With this design, the test sample is made to pass through excess amount of high affinity imatinib-containing capture zone first to avoid trace amounts of binding of nilotinib to wild type BCR-ABL which can otherwise generate false positive results. Use of primary antibody for immunochromatographic affinity binding is unique to this assay and minimizes non-specific molecular interactions that may result in false positives, unlike most of the currently available tools that use secondary antibodies.

Lateral flow immunoassays are simple to use by untrained operators and generally produce a result within 15 minutes. They are very stable and robust, have a long shelf life and do not usually require refrigeration. They are also relatively inexpensive to produce. These features make them ideal for use at the point-of-care and for testing samples in the field, as well as in the laboratory. However, their sensitivity is limited without additional concentration or culture procedures.

While most lateral flow immunoassays are only capable of providing a qualitative result, it is possible to obtain some degree of quantification by measuring the amount of conjugate bound to the capture zone. This can be done using a dedicated reader to measure the intensity of the colored test line. For example, the Neogen Corporation has developed the Accuscan™ lateral flow reader for use with its range of Reveal™ assay kits and Charm Sciences also supplies a reader for its Rosa™ range of mycotoxin test strips.

A diagnostic system in kit form of the present invention includes, for example, a nitrocellulose strip with at least one immobilized drug and Reagent A in an amount sufficient for at least one assay. Such kits may comprise a carrier means being compartmentalized to receive in close confinement one or more container means such as vials, tubes, and the like, each of the container means comprising one of the separate elements to be used in the method. For example, one of the container means may comprise an antibody that is or can be detectably labeled. The kit of the invention will typically comprise the container described above and one or more other containers comprising materials desirable from a commercial and user standpoint, including buffers, diluents, filters, needles, syringes, and package inserts with instructions for use. Instructions for use of the packaged reagent are also typically included. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

Although an antibody has been described throughout as the labeled binding agent, it should be understood that the binding agent could be selected from the group consisting of a DNA aptamer, and RNA aptamer, a protein aptamer, an antibody, an antibody fragment, a binding polypeptide, a binding peptide, and combinations thereof.

As used herein, the terms label refers to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel methods and/or systems.

The invention provides a method for screening a patient for a disease state suitable for imatinib or nilotinib therapy, comprising the steps of: a) obtaining a test sample from the patient; b) combining said test sample with Reagent A, wherein Reagent A comprises a hypotonic KCl solution with a labeled binding agent that binds BCR-ABL; c) incubating the sample and Reagent A for sufficient time such that the labeled binding agent can bind BCR-ABL can form; d) delivering the incubated sample to a carrier containing a membrane with immobilized drug; and e) visually detecting a line on the membrane if the immobilized drug has bound to the labeled binding agent-BCR-ABL complex, wherein the presence of the visual line indicates that the patient will respond to the drug. In some cases, the disease state is CML. In some cases, the immobilized drug is imatinib. In some cases, more than one drug can be immobilized to the membrane. In some cases, imatinib and nilotinib are immobilized to the membrane. In some cases, the labeled binding agent is a gold-labeled anti-BCR-ABL antibody. The method may further include using binding agents that bind other proteins can be included to serve as controls. In some cases, the other proteins are PDGFR and c-kit. In some cases, the labeled binding agents are gold-labeled anti-PDGFR antibody (raised in a species other than the species the anti-BCR-ABL antibody was raised) and gold-labeled anti-c-kit antibody (raised in a species other than the species the anti-BCR-ABL antibody was raised). If controls are used, the membrane also has a strip of immobilized antibodies, wherein the antibodies are against the species the control antibodies were raised and will not bind to the anti-BCR-ABL antibody.

The invention provides a method for monitoring a patient receiving imatinib or nilotinib therapy, comprising the steps of: a) obtaining a test sample from the patient; b) combining said test sample with Reagent A, wherein Reagent A comprises a hypotonic KCl solution with a labeled binding agent that binds BCR-ABL; c) incubating the sample and Reagent A for sufficient time such that the labeled binding agent can bind BCR-ABL can form; d) delivering the incubated sample to a carrier containing a membrane with immobilized drug; and e) visually detecting a line on the membrane if the immobilized drug has bound to the labeled binding agent-BCR-ABL complex, wherein the presence of the visual line indicates that the patient is still responsive to the drug. In some cases, the disease state is CML. In some cases, the immobilized drug is imatinib. In some cases, more than one drug can be immobilized to the membrane. In some cases, imatinib and nilotinib are immobilized to the membrane. In some cases, the labeled binding agent is a gold-labeled anti-BCR-ABL antibody. The method may further include using binding agents that bind other proteins can be included to serve as controls. In some cases, the other proteins are PDGFR and c-kit. In some cases, the labeled binding agents are gold-labeled anti-PDGFR antibody (raised in a species other than the species the anti-BCR-ABL antibody was raised) and gold-labeled anti-c-kit antibody (raised in a species other than the species the anti-BCR-ABL antibody was raised). If controls are used, the membrane also has a strip of immobilized antibodies, wherein the antibodies are against the species the control antibodies were raised and will not bind to the anti-BCR-ABL antibody.

If drug resistance to imatinib and/or nilotinib is detected, an alternative treatment can be dasatinib. Dasatinib is effective against imatinib and nilotinib resistant cancer cells because it is different in structure from both imatinib and nilotinib and binds a different pocket in the BCR-ABL protein. Even if Dasatinib resistance occurs, another treatment option is bosutinib. Another treatment option for nilotinib resistance is ponatinib.

The invention will be further described in the following examples, which do not limit the scope of the invention described in the claims.

EXAMPLES

Example 1—Identification of Imatinib and/or Nilotinib Sensitivity

Figure 6A:
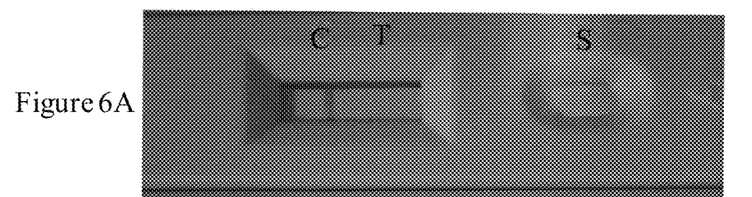
FIGS. 6A-F are photographs of actual test strips showing various outcomes of the lateral flow assay.

FIG. 6A shows a test strip containing the immobilized drug, amino imatinib, that was tested with buffer alone (the same buffer in which is used for cell lysate preparation, described below), which did not contain the recombinant BCR-ABL protein. Two drops of the buffer were added to the sample pad "S". Next two drops of the reagent provided with the strip which comprised hypotonic KCl, gold-conjugated anti-BCR-ABL antibody that was raised in mouse, gold-conjugated anti-c-kit antibody raised in rabbit, and gold-conjugated anti-PDGFR antibody raised in rabbit were added. Since the sample did not contain the recombinant BCR-ABL protein, the test lane "T" did not show a band. The control lane "C" which had the secondary antibody against BCR primary antibody immobilized the colloidal gold conjugated anti-BCR antibody, gave a color in lane "C" and showed the test was working. This experiment served as a negative control experiment, demonstrating that the test strip did not give false positive results.

Figure 6B:
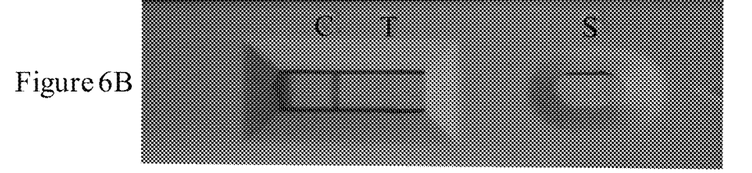

Next, a leukemia cell line (K 562) known to contain the recombinant BCR-ABL protein was used to test if the kit detects the recombinant BCR-ABL protein. The K 562 cell line was grown on a 100 mm cell culture dish and was lysed with 1 ml of phospho lysis buffer. Two drops of the cell lysate was added to the sample pad "S" in FIG. 6B. Then, two drops of the running reagent (comprised of hypotonic KCl, gold-conjugated anti-BCR-ABL antibody that was raised in mouse, gold-conjugated anti-c-kit antibody raised in rabbit, and gold-conjugated anti-PDGFR antibody raised in rabbit) provided with the test strip was added. The recombinant BCR-ABL protein in the lysate was bound by the immobilized imatinib in the test lane "T" and resulted in a visible band in the test lane "T". Thus, this experiment served as a positive control as it showed that the test strip is capable of detecting BCR-ABL protein. The control lane "C", which has the secondary antibody against BCR primary antibody, immobilized the colloidal gold conjugated anti-BCR antibody gave color in lane "C" confirmed the assay is working.

Figure 6C:
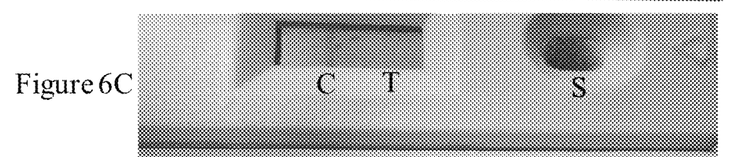

A blood sample from a normal male human was used to see if the assay gives false positive results. Two drops of blood from a normal male human who did not have leukemia was dropped onto the sample pad "S". Then two drops of the running reagent provided with the test strip was added to the sample pad, as described above. The contents migrated along the lateral flow membrane and since the blood was devoid of BCR-ABL protein (since the human did not have leukemia); the imatinib immobilized in test lane "T" did not bind to any of the sample. Therefore, no color appeared in test lane "T" (FIG. 6C). This again confirmed the test strip did not provide false positive results. The control lane "C" which had the secondary antibody against BCR primary antibody immobilized the colloidal gold conjugated anti-BCR antibody, giving a color in lane "C" and showed the test was working.

Figure 6D:
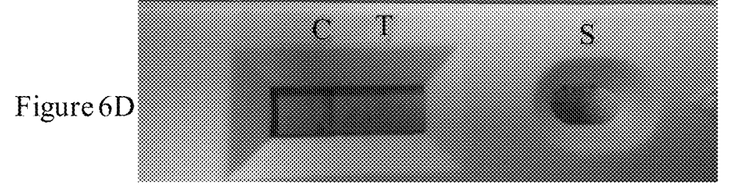

A human male individual found to be suffering from Chronic Myeloid Leukemia was identified and two drops of his blood was dropped onto the sample pad "S". Two drops of the running reagent (as described above) was added. Since the blood of the male human had the BCR-ABL protein, the sample was bound by the imatinib immobilized in the test lane "T", as seen in FIG. 6D. This was detected by the colloidal gold conjugated antibody against BCR protein, thus giving a band in test lane "T". This test showed that the test strip is capable of detecting BCR-ABL in blood samples of a human with CML. The control lane "C" which had the secondary antibody against BCR primary antibody immobilized the colloidal gold conjugated anti-BCR antibody, giving a color in lane "C" and showed the test was working.

Figure 6E:
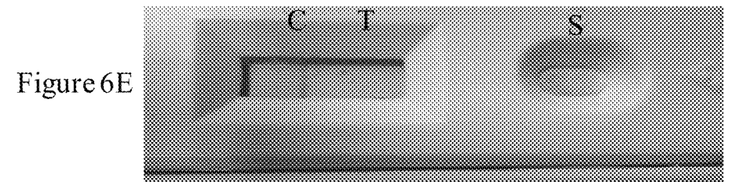

A blood sample from a normal female human was also tested. Two drops of blood from a normal female who did not have leukemia was dropped onto the sample pad "S". Then two drops of the running reagent (as described above) provided with the test strip was added to the sample pad. The contents migrated along the lateral flow membrane and since the blood was devoid of BCR-ABL protein, the imatinib immobilized in test lane did not bind the sample. Therefore, as shown in FIG. 6E, no color was visible in the test lane "T". This again confirmed the test strip did not provide false positive results. The control lane "C" which had the secondary antibody against BCR primary antibody immobilized the colloidal gold conjugated anti-BCR antibody giving a color in lane "C" showed the test was working.

Figure 6F:
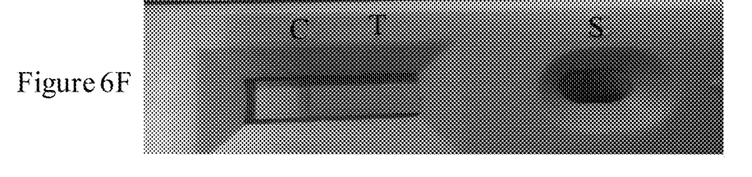

A human female individual found to be suffering from Chronic Myeloid Leukemia was identified and two drops of her blood was dropped onto the sample pad "S". Two drops of the running reagent (as described above) was added. Since the blood of the female human had the BCR-ABL protein, the sample was bound by the imatinib immobilized in the test lane "T", as seen in FIG. 6F. This was detected by the colloidal gold conjugated antibody against BCR protein, thus giving a band in test lane "T". This test showed that the test strip is capable of detecting BCR-ABL in blood samples of a human with CML. The control lane "C" which had the secondary antibody against BCR primary antibody immobilized the colloidal gold conjugated anti-BCR antibody, giving a color in lane "C" and showed the test was working.

The experiments performed with results shown in FIGS. 6C-6FE were done to show that the test strip worked in blood sample of different sexes without any interference.

Example 2—Detection of Other Drug Resistance

Although the previous example concerns the demonstration of the exemplary embodiment of imatinib and/or nilotinib resistance, the present invention may be utilized for the detection of drug resistance in other diseases. In some embodiments, the drug is an inhibitor of a different protein kinase. The kinase may or may not be a fusion protein that results from a chromosomal translocation. In other cases, the therapeutic target is a protein that is not a kinase. As one skilled in the art can recognize, this assay will be effective in detecting drug resistance in any disease provided that the drug can be immobilized to a substrate such as a nitrocellulose membrane and the drug resistance is mediated by alterations in the drug binding site on the therapeutic target protein.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A kit for detecting drug resistance in a disease, wherein said kit comprises:
  a. a substrate comprising at least one control zone and at least one capture zone, wherein the at least one control zone comprises a secondary antibody that is immobilized on said substrate wherein the at least one secondary antibody is specific for at least one labeled antibody that binds a protein selected from a group consisting of Platelet-derived growth factor receptor (PDGFR) and c-tyrosine kinase receptor (c-kit), and
    wherein the at least one capture zone comprises at least one drug that is immobilized on said substrate and the drug is selected from a group consisting of Imatinib and Nilotinib; and
  b. a reagent comprising at least one labeled antibody that binds to BCR-ABL,
  and at least one labeled antibody that binds to the at least one protein of (a), wherein the at least one secondary antibody and at the least one antibody that binds to BCR-ABL are raised in different animal species.
2. The kit of claim 1, wherein said at least one labeled antibody that binds to BCR-ABL is a gold-labeled anti-BCR-ABL antibody and wherein said at least one labeled antibody that binds one protein of (a) is selected from the group consisting of gold-labelled anti-PDGFR antibody and gold-labelled anti-c-Kit antibody.
3. The kit of claim 1, wherein the disease is chronic myeloid leukemia.

* * * * *